United States Patent
Kumar et al.

(10) Patent No.: US 6,792,943 B2
(45) Date of Patent: Sep. 21, 2004

(54) INTUBATING VENTILATORY FACE MASK

(75) Inventors: Matthew M. Kumar, Oronoco, MN (US); Larry D. Johnson, Red Wing, MN (US)

(73) Assignee: Minnesota High-Tech Resources, LLC, Red Wing, MN (US)

( * ) Notice: Subject to any disclaimer, the term of this patent is extended or adjusted under 35 U.S.C. 154(b) by 350 days.

(21) Appl. No.: 10/037,037

(22) Filed: Oct. 25, 2001

(65) Prior Publication Data

US 2003/0047189 A1 Mar. 13, 2003

Related U.S. Application Data

(60) Provisional application No. 60/317,258, filed on Sep. 5, 2001.

(51) Int. Cl.[7] .............................................. A61M 16/00
(52) U.S. Cl. ............................... 128/200.26; 128/205.25
(58) Field of Search ....................... 128/200.26, 202.28, 128/202.29, 203.11, 205.25, 206.11, 206.15, 206.21, 206.26, 206.28, 206.29, 207.12, 207.13, 207.14, 207.15, 207.16, 207.18

(56) References Cited

U.S. PATENT DOCUMENTS

| | | | |
|---|---|---|---|
| 3,905,361 A | * | 9/1975 | Hewson et al. ........ 128/202.16 |
| 4,328,797 A | * | 5/1982 | Rollins et al. ......... 128/202.27 |
| 4,498,834 A | | 2/1985 | Christiansen |

(List continued on next page.)

FOREIGN PATENT DOCUMENTS

WO    WO 92/13587    8/1992

OTHER PUBLICATIONS

Article: "Fibreoptic Bronchoscopy in Sedated Infants Facilitated by an Airway Endoscopy Mask" by T. Erb, M.D., et al, 1999 Blackwell Science, Ltd., *Paediatric Anaestesia*, 1995, 9:47–52; *Article*: "Use of a Lighted Stylet for Tracheal Intubation Through an Intubating Port of a Mask", by R. Uda, M.D., Ph.D., et al, *Anaesthesiology*, v. 91, No. 5, Nov. 1999, p. 1560.
Article: "The Airway Endoscopy Mask: Useful Device for Fibreoptic Evaluation and Intubation of the Paediatric Airway", by F. Frei, M.D., et al, 1995 Arnette Blackwell SA, *Paediatric Anaesthesia 1995, 5:319–324*; VBM Endoskopiemaske Anesthesia, Endoscopy Mask, *Website*: VBM Medizintechnik GmbH (e–mail: Info@VBM–medical.de).

*Primary Examiner*—Henry Bennett
*Assistant Examiner*—Teena Mitchell
(74) *Attorney, Agent, or Firm*—Fredrikson & Byron P.A.

(57) ABSTRACT

Apparatus and methods for providing simultaneous positive pressure ventilation to a patient together with introduction of medical device shafts into the trachea, esophagus, and/or nasal cavity of a patient. A face mask according to present invention can be used to provide positive pressure ventilation and delivery of general anesthesia gas while maintaining an airtight seal about the face, simultaneous with the introduction of a medical device shaft, for example, a fiber optic laryngoscope, into the trachea of a patient. The mask can include a standard breathing circuit port and a second instrument port having a controllably variable or adjustable inside diameter for providing a tight seal about the inserted medical device shaft. One mask has an inflatable and deflatable cuff disposed within the inside tubular walls of the instrument port. The mask may be used in a difficult airway situation, to provide positive pressure ventilation and general anesthesia gas to a critically injured patient, allowing an anesthesiologist to identify the trachea with a fiber optic laryngoscope, and advance an endotracheal breathing tube over the fiber optic laryngoscope, while maintaining an airtight seal between the controllably variable inside diameter instrument port and the inserted medical device shafts. The instrument port may later be opened or dilated to allow the mask to be passed over the proximal end of the endotracheal tube, requiring only brief interruption in positive pressure ventilation.

33 Claims, 7 Drawing Sheets

U.S. PATENT DOCUMENTS

| | | | | |
|---|---|---|---|---|
| 4,537,192 A | * | 8/1985 | Foster | 128/207.17 |
| 4,580,556 A | | 4/1986 | Kondur | |
| 4,598,741 A | | 7/1986 | Johnson et al. | |
| 5,197,463 A | | 3/1993 | Jeshuran | |
| 5,257,636 A | * | 11/1993 | White | 128/897 |
| 5,285,778 A | | 2/1994 | Mackin | |
| 5,400,781 A | * | 3/1995 | Davenport | 128/206.28 |
| 5,431,158 A | | 7/1995 | Tirotta | |
| 5,474,060 A | * | 12/1995 | Evans | 128/204.22 |
| 5,485,837 A | * | 1/1996 | Solesbee et al. | 128/207.17 |
| 5,607,386 A | | 3/1997 | Flam | |
| 5,664,594 A | | 9/1997 | Kee | |
| 5,694,929 A | | 12/1997 | Christopher | |
| 5,964,217 A | | 10/1999 | Christopher | |
| 6,070,581 A | | 6/2000 | Augustine et al. | |
| 6,189,533 B1 | | 2/2001 | Simon et al. | |
| 6,196,225 B1 | | 3/2001 | Allgeyer | |
| 6,257,236 B1 | | 7/2001 | Dutkiewicz | |
| 6,405,725 B1 | * | 6/2002 | Christopher | 128/200.26 |
| 6,631,713 B1 | * | 10/2003 | Christopher | 128/200.21 |
| 2003/0024533 A1 | * | 2/2003 | Sniadach | 128/205.25 |

* cited by examiner

INTUBATING VENTILATORY FACE MASK

RELATED APPLICATIONS

This application claims priority to U.S. Provisional Application No. 60/317,258, filed Sep. 5, 2001, titled INTUBATING VENTILATORY FACE MASK, herein incorporated by reference.

FIELD OF THE INVENTION

The present invention is related generally to medical devices. More specifically, the present invention relates to face masks which can find one use in delivery of anesthesia and respiratory gases. The present invention includes a standard breathing circuit port and a variable inside diameter port which can be used to form an airtight seal about fiberoptic laryngoscopes and endotracheal tubes.

BACKGROUND OF THE INVENTION

The use of endotracheal tubes or breathing tubes is the preferred and standard method for administering general anesthesia for major surgical procedures. The endotracheal tube typically has a distal end carrying an inflatable balloon disposed about the circumference. The balloon can be inflated to form an air tight seal within the trachea once the endotracheal tube distal end is in place. The proximal end of the endotracheal tube typically has a standard connector, having nominally $3/8^{th}$ inch inside diameter and $5/8^{th}$ inch outside diameter. The endotracheal tube may be put into position by an anesthesiologist, the distal balloon inflated, and the oxygen and anesthesia gases delivered to the patient. The endotracheal tube is typically put into position after the patient has been put under, to avoid patient gagging on the inserted endotracheal tube.

Some patients present "difficult airway situations." These situations make it difficult to place the endotracheal tube. Examples of difficult airway situations include patients having short muscular necks, receding lower jaws with obtuse mandibular angle, limited cervical spine mobility, and poor mobility of the mandible. Extremely obese patients may also present a difficult airway situation. In a difficult airway situation, an anesthesiologist may be forced to use a flexible fiberoptic scope to identify or locate the proper position for the endotracheal tube, followed by coaxially sliding the endotracheal tube over the pre-positioned fiber optic tube.

One exemplary scenario illustrates one set of problems addressed by the present invention. A patient is wheeled into an emergency room, in critical condition, having been involved in an automobile accident. The patient has significant internal injuries with internal bleeding, requiring immediate surgery. The patient's neck has been fractured in the accident, and significant movement of the neck may render the patient quadriplegic for the remainder of their life.

If the anesthesiologist tilts the head backward to insert the breathing tube to begin general anesthesia, the patient may be rendered paraplegic. If the anesthesiologist does not insert the breathing tube, general anesthesia, and therefore surgery, cannot be begun. One solution is to perform a tracheotomy. This can include cutting the patient's neck and inserting an endotracheal tube through the front of the neck. While the patient's skin may be numb, the cutting will generally be performed prior to the administration of general anesthesia, while the patient is awake. This is a less than optimal situation for the still awake, and injured patient.

One method to address the above situation includes inserting a fiberoptic laryngoscope to identify the trachea, followed by the insertion of the endotracheal tube over the laryngoscope. If the fiberoptic laryngoscope were inserted with no sedation or general anesthesia, the patient's gag reflex and general panic may result in the patient gagging, biting through the fiberoptic laryngoscope, and even vomiting, with the possible aspiration or inhalation of vomit and resultant suffocation. All this is occurring prior to proper placement of the endotracheal tube, before the required major medical procedure has even begun.

In order to deal with the above mentioned problems, the anesthesiologist may be required to sedate the patient simply to insert the fiberoptic tube and/or endotracheal tube. When the patient is sedated, the reaction of the patient may be highly variable and unpredictable. A dose of a sedative, for example, sodium pentathol, may leave one patient awake and thrashing, while causing the complete cessation of breathing in another patient. If too low a dose is initially given, the time elapsed before placement of the breathing tube and the initiation of surgery is increased. If too high a dose of sedative is given to the patient, breathing will stop, with death eminent unless positive pressure ventilation can be begun. Positive pressure ventilation through the endotracheal tube could be initiated if the endotracheal tube were in place. Unfortunately for the patient, that is not the case.

The anesthesiologist facing this difficult situation may thus be faced with a patient thrashing about while the fiberoptic probe is inserted into his trachea, or faced with the situation where the patient has ceased breathing and has no endotracheal tube yet in place.

General anesthesia gases may be delivered through a standard, soft sealing face mask. However, this standard face mask must be removed in order to insert the fiberoptic laryngoscope, thereby ceasing delivery of the anesthesia gas. If the patient has ceased breathing due to the sedative previously administered, a standard face mask may be used to provide positive pressure ventilation, forcing enriched oxygen gases into the patient's lungs. However, when the standard face mask is removed, the patient no longer breathes, and the blood oxygen level drops or desaturates, along with any delivered general anesthesia gas. Once the standard face mask is removed, the anesthesiologist is under intense time pressure to properly position the fiberoptic laryngoscope and the endotracheal tube. The time required to properly place the fiberoptic laryngoscope and the endotracheal tube is time in which the patient is not receiving any general anesthesia gas and is not receiving any oxygen. If the procedure is too difficult and requires too much time, the patient may awaken due to lack of anesthesia gases and/or approach death due to lack of oxygen.

What would be desirable is a sealing face mask which permits simultaneous positive pressure ventilation, delivery of anesthesia gases, and also allows simultaneous placement of medical shafts such as fiberoptic probes and endotracheal tubes, together with maintenance of positive pressure and delivery of oxygen to the patient. What would be advantageous is a face mask which permitted simultaneous introduction of numerous diagnostic and therapeutic devices into the mouth and nose of a patient concurrent with the delivery of positive pressure ventilation.

SUMMARY OF THE INVENTION

The present invention provides intubating ventilatory face mask apparatus and methods. One face mask includes a central region surrounded by a peripheral soft seal region. A breathing circuit port can be disposed on the mask as well as an instrument port. The instrument port can have a controllably variable or adjustable inside diameter. The instrument port inside diameter can be controlled through the increase and decrease of the inside diameter of the sealing wall of an instrument cuff or envelope disposed within the instrument port. In one mask, an inflatable envelope or balloon material is disposed within a short, tubular, instrument port lip or wall. The cuff can be inflated and deflated through an attached valve or port. One mask is adapted to receive a standard syringe to inflate and deflate the instrument port cuff. A snap fit lid can be provided for sealing the instrument port when its use is not required. The inside diameter of the instrument port is preferably adjustable between a size small enough to form an air tight seal about a fiber optic laryngoscope, and a size large enough to allow passage of the proximal connector of an endotracheal tube. In one embodiment, the inside diameter of the instrument port is controlled through an iris mechanism, analogous to that found in camera lenses.

One mask has an internal volume of between about 100 and 150 cubic centimeters. The instrument port is preferably centrally located with respect to the apex of the mask conical area or dome. The standard breathing circuit port is preferably located off-center, being located further off-center relative to the instrument port. The centrally disposed instrument port can better provide access to the nose and mouth.

The present invention includes a method for providing a breathable gas to a patient. One method includes providing a mask having a first aperture and a second aperture, with the first aperture having a controllably variable or adjustable inside diameter. The second aperture can be in fluid communication with the breathable gas. The method includes placing the mask on the face of the patient, and can include forming an airtight seal between the face and the mask. The method further includes supplying the breathable gas to the patient through the second aperture, and inserting a first shaft member through the first aperture. The first aperture can be closed about the inserted first shaft member, with airtight seal being formed in some methods between the shaft and first aperture walls. The first shaft member can be advanced into the mouth, nose, trachea, or esophagus of the patient, while supplying the breathable gas to the patient.

In some methods, the supplying step includes supplying the breathable gas at a positive pressure to the patient between the face and mask. The breathable gas can be enriched in oxygen and may include anesthetic gases. In some methods, the first shaft member is a fiber optic laryngoscope and the method further includes identifying or locating the trachea. The method may include providing a second shaft member having a lumen at least partially therethrough, and advancing the second shaft lumen over the first shaft, through the mask first aperture and into the patient. The method may further include the second shaft being an endotracheal tube, the method further including supplying the breathable gas through the breathing tube and removing the mask from the face region of the patient over the endotracheal tube. The mask may be removed over the endotracheal tube even where the endotracheal tube has a proximal connector and the proximal connector is passed through the variable sized first aperture.

The present invention may be used in difficult airway situations, where it is desirable to place a breathing tube into the trachea of a patient, and where a fiber optic laryngoscope is preferably used to identify the trachea, followed by advancing an endotracheal tube over the positioned fiber optic laryngoscope. The mask may be positioned over the face of a patient, and positive pressure ventilation and delivery of general anesthesia gas begun immediately. A fiber optic laryngoscope may be advanced through the first, adjustable inside diameter aperture while maintaining an airtight seal between the fiber optic laryngoscope and the adjustable inside diameter aperture.

With the trachea identified, the endotracheal tube may be passed over the prepositioned fiber optic laryngoscope, and the adjustable inside diameter of the first aperture increased to allow passage of the endotracheal tube, while maintaining an airtight seal between the endotracheal tube outer wall and the inner wall of the first aperture. The endotracheal tube can be positioned within the trachea, and the fiber optic laryngoscope removed, all while maintaining positive pressure and delivery of breathable gas to the patient. With the endotracheal tube in place, the mask controllably variable sized first aperture may be dilated, for example, by evacuating the gas from an inflatable cuff. With the inside diameter of the first aperture increased, the mask may be removed over the proximal end of the endotracheal tube. The breathing circuit may be then coupled directly to the proximal connector of the breathing tube, and breathable gases delivered through the endotracheal or breathing tube.

In some exemplary and non-limiting uses of the invention, the mask may be used in procedures including the examination and treatment of lesions of the nose, sinuses, mouth, larynx, pharynx, trachea, bronchi, esophagus and stomach. In one beneficial use of the present invention, the mask may be carried in an ambulance, and applied to the face of an accident victim, with the variable sized first aperture initially covered with a lid. A breathable gas may be delivered through the second aperture. If it is necessary to introduce a breathing tube, the lid may be removed, the inside diameter of the first aperture increased or decreased, and the fiber optic laryngoscope and/or breathing tube inserted through an airtight seal formed between the inserted shaft and the variable inside diameter aperture. The positive pressure provided by the mask and the breathable gas delivered through the mask need only be momentarily discontinued when the mask is lifted free of the positioned breathing tube. The same mask may thus remain in position from the initial placement in the ambulance until the breathing tube has been successfully positioned within a hospital.

DETAILED DESCRIPTION OF THE PREFERRED EMBODIMENTS

The following detailed description should be read with reference to the drawings, in which like elements in different drawings are numbered identically. The drawings, which are not necessarily to scale, depict selected embodiments and are not intended to limit the scope of the invention. Several forms of invention have been shown and described, and other forms will now be apparent to those skilled in art. It will be understood that embodiments shown in drawings and described above are merely for illustrative purposes, and are not intended to limit scope of the invention as defined in the claims which follow.

Figure 1:
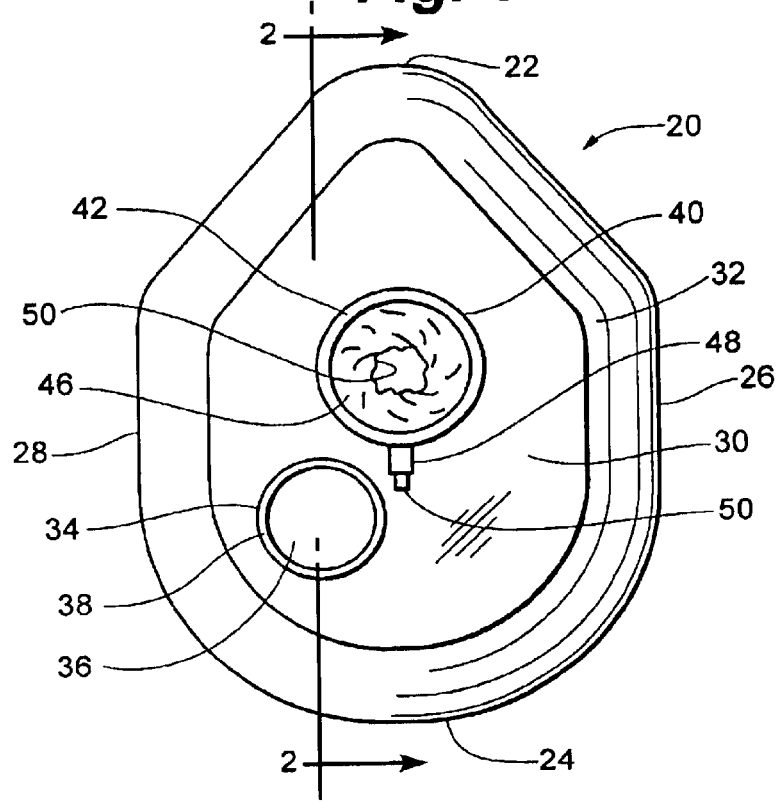
FIG. 1 is a front view of one face mask according to the present invention.

Referring now to FIG. 1, a face mask 20 is illustrated, having generally a top 22, a bottom 24, a right side 26, and a left side 28. Mask 20 includes generally a central conical or dome region 30, surrounded by a soft peripheral seal region 32. Central dome 30 may be formed of a transparent, plastic or resin material. Soft seal 32 may often be an air filled envelope, to provide an adjustable tight seal against the face of the patient. Soft seal 32 often has an inflation valve which can be filled with air using a syringe.

Mask 20 includes a standard breathing circuit port or aperture 34. Breathing circuit aperture 34 includes a wall 38 defining a lumen 36 within. Breathing circuit aperture 34 is preferably standard size to adapt to standard size breathing circuit tubes. Breathing circuit aperture 34 may be used to allow passage of positive pressure ventilation gases and the exhaled gases of the patient.

Mask 20 also includes a variable inside diameter port or aperture 40. Variable inside diameter aperture 40 has a controllably variable inside diameter. "Controllably variable inside diameter" as used herein, means an inside diameter which may be increased or decreased about the patent or open lumen extending through the aperture inner walls. Aperture 40 may also be described as having an adjustable inside diameter, or having a seal having an adjustable inside diameter. "Controllably variable inside diameters" and "adjustable inside diameters" may be contrasted with distensible membrane apertures having distensible or elastically expandable inside diameters. The distensible apertures are not variable in diameter about an open, unoccupied lumen, but require a shaft inserted through the membrane aperture lumen to stretch the opening inside diameter about the inserted shaft. Aperture 40 may also be referred to as the "instrumentation aperture", as it may be used to introduce various instruments, other than simply breathable gases.

Aperture 40 includes generally a tubular wall or lip 42, and a seal, an inner wall 50 which forms the inside diameter. Aperture 40 can include an inflatable cuff, envelope, or balloon 46. Inflatable cuff 46 may be formed from a single, torroidal shaped balloon material, or may be formed from multiple sections or leaflets of inflatable materials. Aperture 40, in the embodiment illustrated, includes an inflation valve 48 having a proximal opening 50. Inflation valve 48 may be used to inject or withdraw inflation gas to vary the inside diameter of aperture 40.

In a preferred embodiment, the breathing circuit port is disposed off center relative to the instrumentation port. In one embodiment, the instrument port is centrally and symmetrically located on the mask. The breathing circuit port can be located off center, or further from the center than the instrument port. In various embodiments, the instrument port can have a maximum inside diameter of about 1 inch, 1.25 inch, 1.50 inch, 1.75 inch, and 2 inches, respectively. The instrument port inside diameter is preferably dimensioned so as to allow the proximal end or connector of a breathing tube to pass through the instrument port. In a preferred embodiment, the instrument port has a maximum inside diameter of about 1.25 inches to 2.0 inches.

Figure 2:
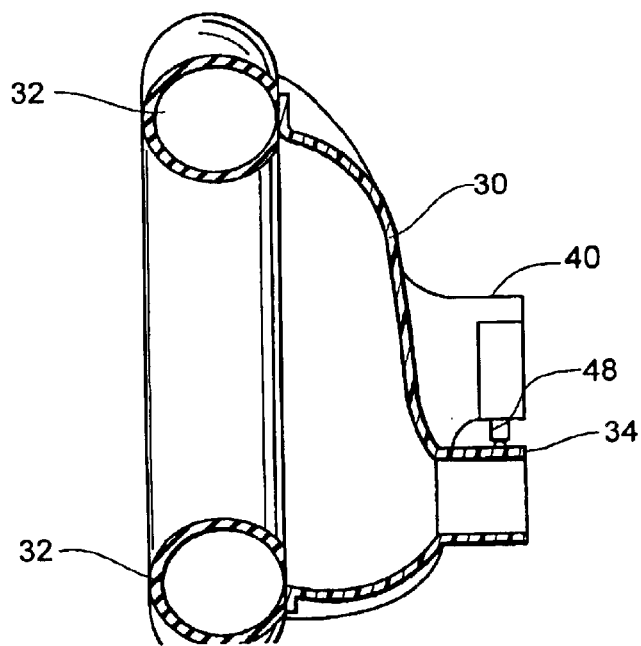
FIG. 2 is a side, cross-sectional view of the mask of FIG. 1.

Referring now to FIG. 2, mask 20 may be viewed from the side. Central dome 30 may be seen to be disposed within outer soft seal 32. Instrumentation port 40 and breathing circuit port 34 are as described above with respect to FIG. 1. In some embodiments, instrumentation port 40 may be covered with a snap-on lid, to seal the port when use of the instrument port is not desired.

Figure 3:
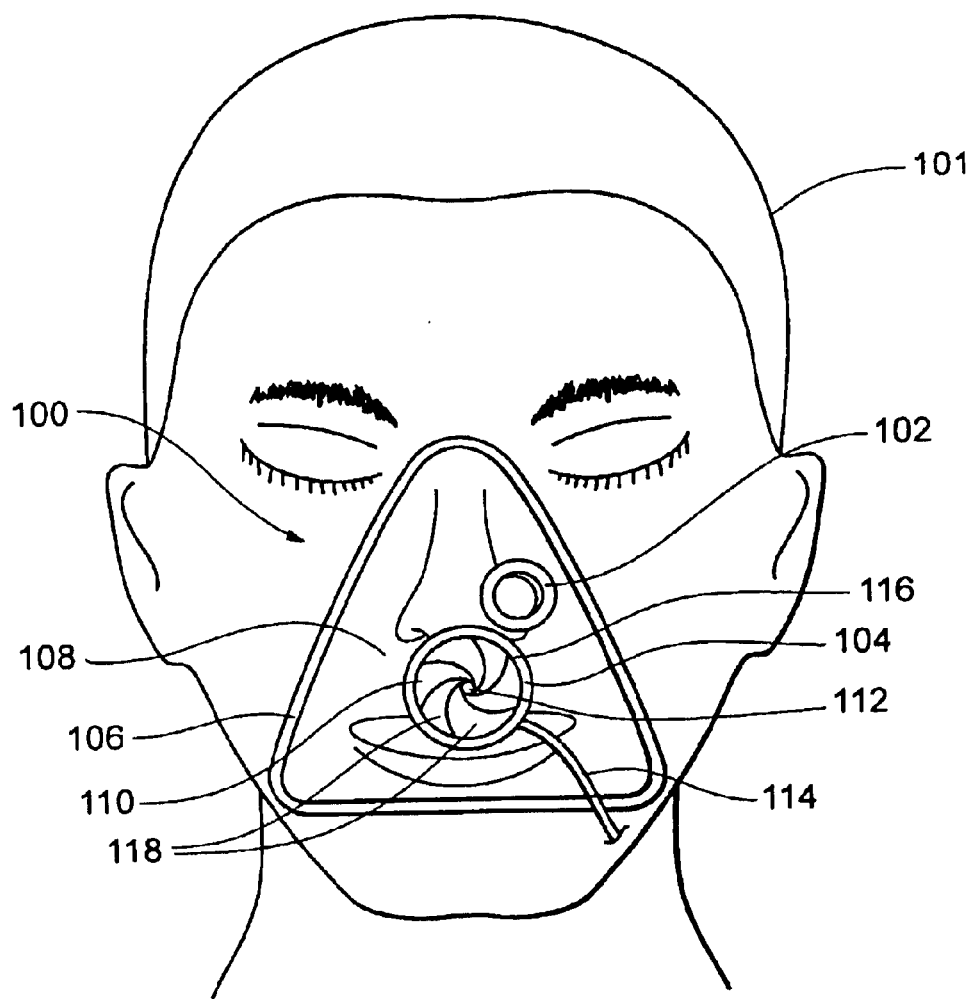
FIG. 3 is a front view of a mask having an iris type variable inside diameter instrument port.

Referring now to FIG. 3, another face mask 100 is illustrated, disposed on the face of a patient 101. Mask 100 may be seen to have generally a central dome 108 disposed within a peripheral soft seal 106. A breathing circuit port 102 may be seen, disposed above and to the right of a more centrally disposed instrument port 104. Instrument port 104 is disposed within a tubular port wall 116. Instrument port 104 includes an iris 110 for varying the inside diameter of a central aperture or lumen 112. Iris 110 may be seen to be formed of numerous elements or leaflets 118. Iris 110 can be controlled by an inside diameter control cable 114. Iris 110 may be formed and controlled in a manner similar to the iris of a camera aperture. Instrument port 104 may be capped by a snap fit lid, when not in use. Control cable 114 may vary depending on the operating mechanism of iris 110. The mechanism may, for example, be electronic or pneumatic.

Figure 8:
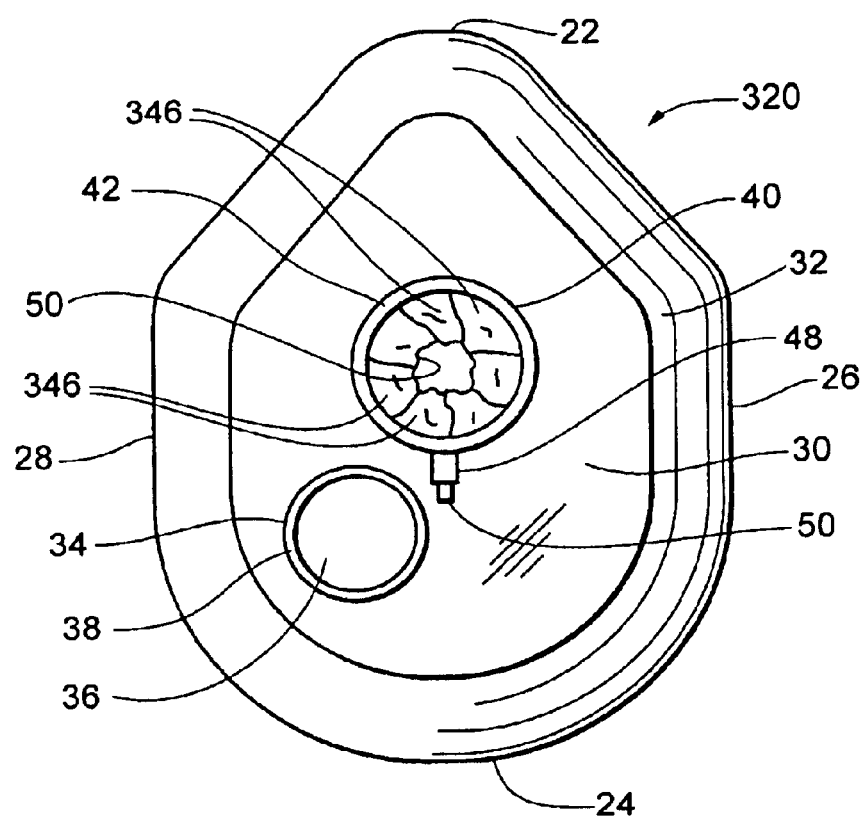
FIG. 8 is a front view of a mask similar to that of FIG. 1, but having multiple inflatable balloons disposed about the central orifice.

FIG. 8 illustrates another mask 320, similar to mask 20 of FIG. 1. Mask 320 includes multiple inflatable balloons 346 in place of the corresponding element 46 in FIG. 1. FIG. 8 also includes similar, identically numbered elements as discussed with respect to FIG. 1.

Figure 4:
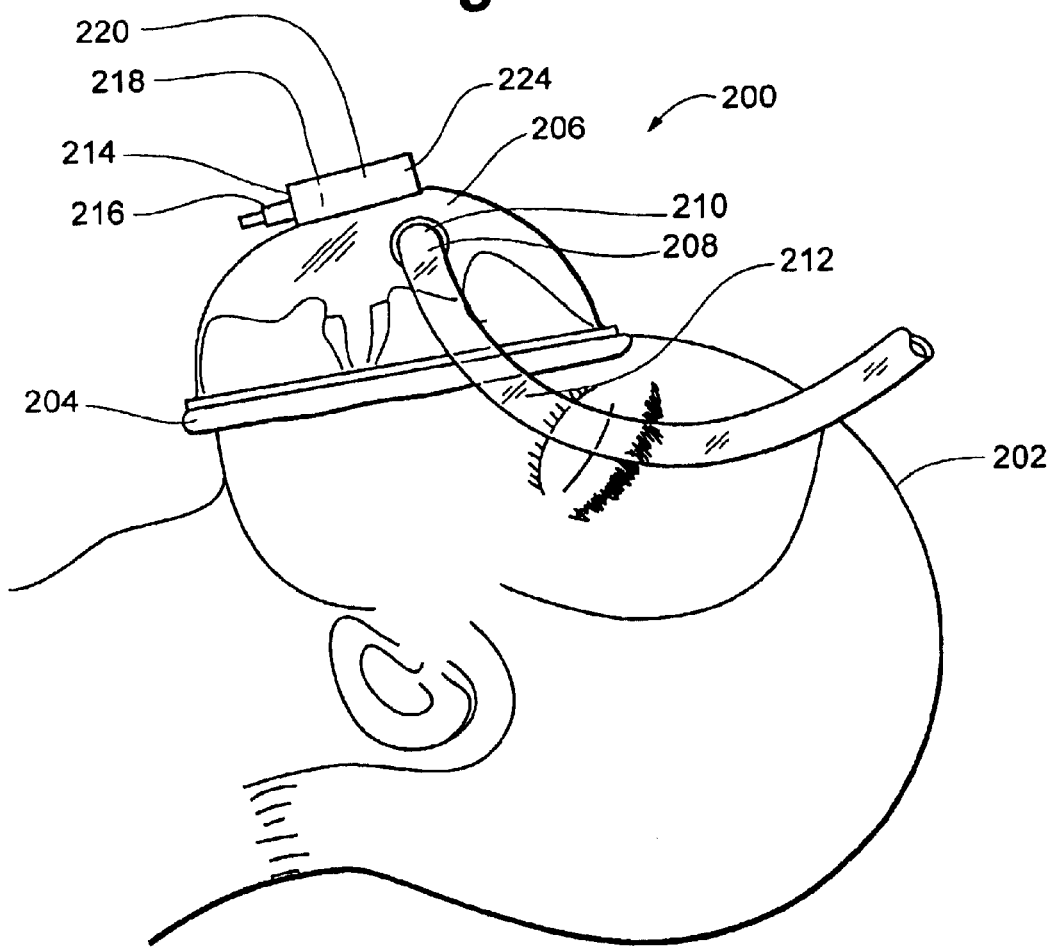
FIG. 4 is a side, perspective view of another mask according to the present invention, disposed on a patient's face and a having breathing circuit tube coupled to the breathing circuit port.

Referring now to FIG. 4, a mask 200 is illustrated, disposed on the face of a patient 202. Mask 200 may be seen to have generally a clear dome or central conical portion 206, disposed within a surrounding peripheral soft seal 204. Mask 200 may be seen to have a breathing circuit port 208 having a tubular wall 210 thereabout. Breathing circuit port 208 may be seen to have a breathing circuit tube 212 coupled to breathing circuit port 208.

Mask 200 also has an instrument port 214 having a tubular wall 224 thereabout and an inflatable cuff 218 therein. Inflatable cuff 218 is coupled to an inflation valve 216 which may be seen extending from the side of instrument port wall 224. Instrument port 214 includes a lumen or central aperture 220 therethrough, the inside diameter which may be varied through the inflation or deflation of cuff 218. A lid maybe snap fit over instrument port 214, when use of the port is not desired. Mask 200 may thereby be used as a typical facemask, when the additional features are not required. In one embodiment, dome 206 has an internal volume of about 150 cubic centimeters.

Figure 5:
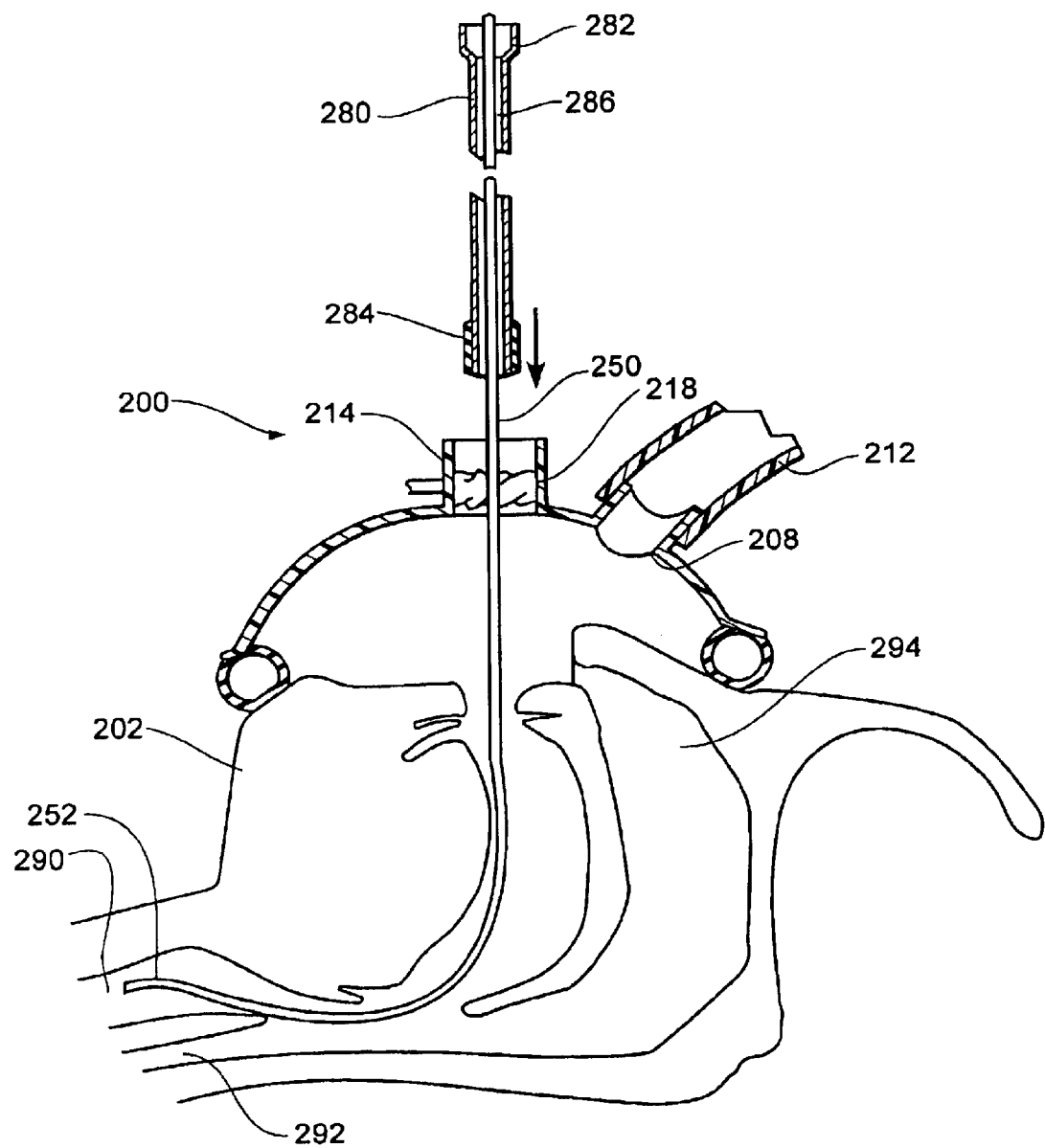
FIG. 5 is a schematic, transverse, cross-sectional view of the mask of FIG. 4, having a fiber optic laryngoscope disposed within an endotracheal tube and inserted through the inflated cuff of the instrument port and into the larynx of the patient.

Referring now to FIG. 5, mask 200 may be seen in cross-section, disposed again on the face of the patient 202. Mask 200 is as described with respect to FIG. 4. Breathing circuit port 208 may be seen coupled to breathing circuit tube 212. A fiber optic laryngoscope 250 may be seen disposed through instrument port 214, through an airtight seal formed between fiber optic tube 250 and inflated cuff 218. Fiber optic tube 250 may be slide through a tightly sealed and partially inflated cuff 218. Fiber optic tube 250 may be seen to have a distal end 252, disposed within a larynx 290. Fiber optic laryngoscope distal tip 252, in other medical procedures, may be inserted within the esophagus 292 or nasal cavity 294.

FIG. 5 illustrates but one use of mask 200. In one aspect, fiber optic tube 250 represents any shaft which my be inserted through mask instrument port 214. In some methods, inflatable cuff 218 may be lubricated to allow easier passage and/or a better seal between the inserted shaft and the variable inside diameter cuff. It should be noted, with respect to FIG. 4, that general anesthesia and positive pressure ventilation may already have begun for the patient illustrated in FIG. 4, reducing the concern about the possibility of anesthesia induced cessation of spontaneous breathing. Once larynx 290 has been identified or located by fiber optic distal end 252, the endotracheal tube may be inserted.

An endotracheal tube 280 may be seen disposed about fiber optic laryngoscope 250. Endotracheal tube 280 may be seen to have a proximal end coupling 282 and a distal end inflatable outer cuff 284. Endotracheal tube 280 may also be seen to have a lumen 286 extending therethrough, which can be used to receive fiber optic laryngoscope 250. It should be noted that during the procedure depicted in FIG. 5, the patient may still be receiving general anesthesia gas and oxygen delivered under pressure. Thus, even if the general anesthesia has caused apnea or the cessation of voluntary breathing, positive pressure ventilation may be provided through breathing circuit tube 212. The treating physician thus has fewer concerns and less time pressure to adequately place the fiber optic laryngoscope.

Figure 6:
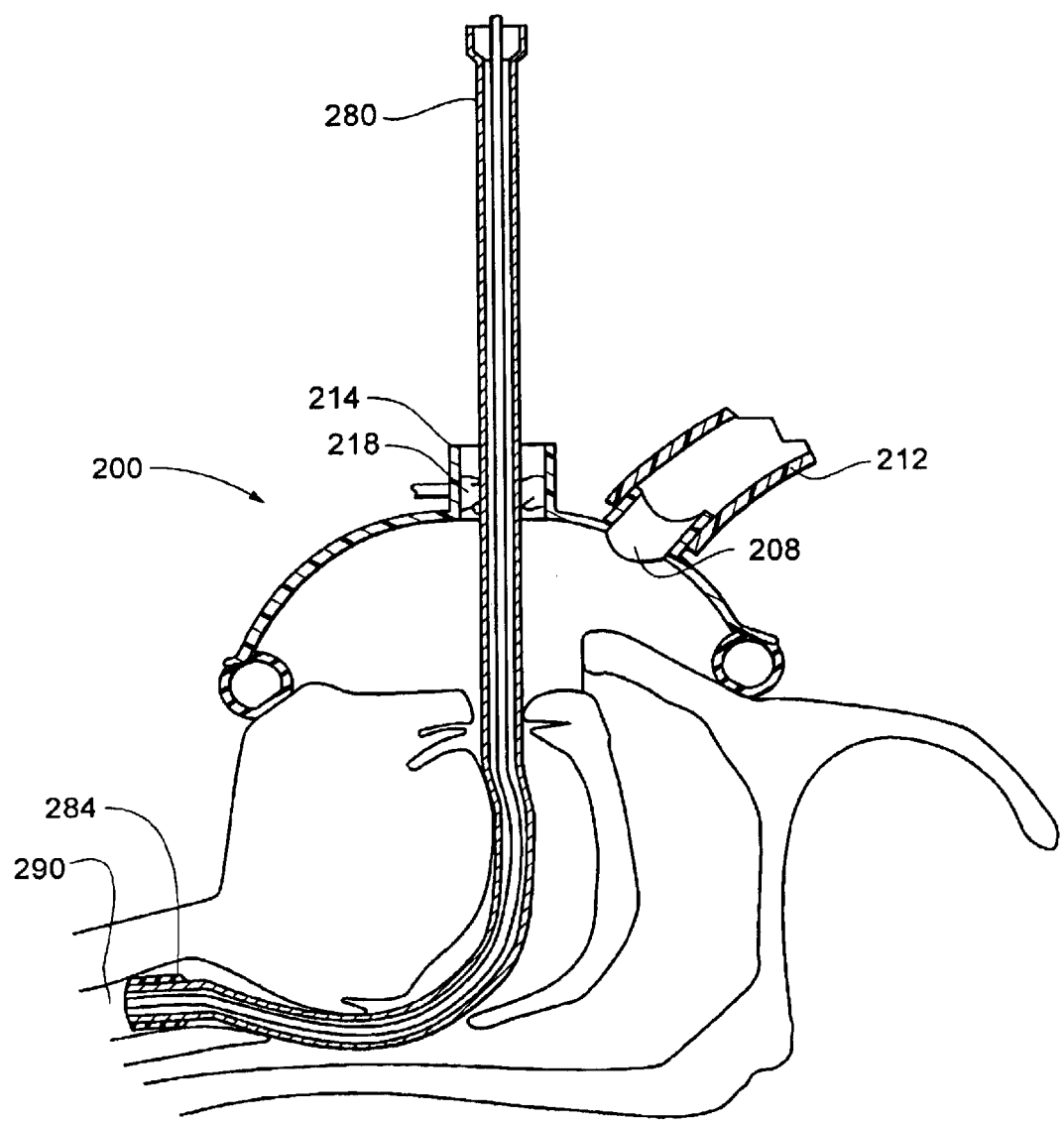
FIG. 6 is a side, transverse, cross-sectional view as in FIG. 5, after the endotracheal tube has been passed through the instrument port, over the fiber optic laryngoscope, and into the larynx of the patient.
Figure 7:
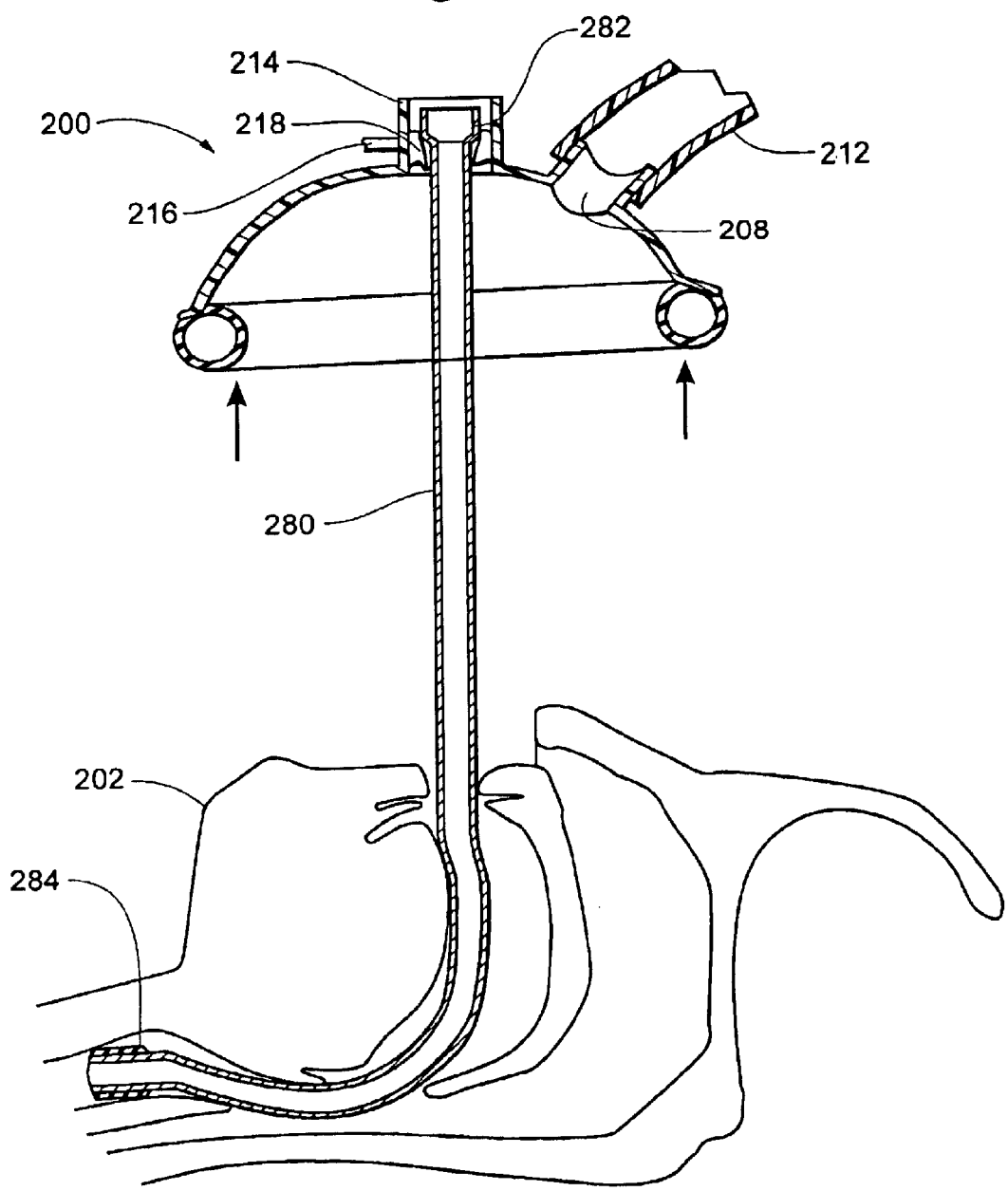
FIG. 7 is a side, transverse, cross-sectional, view as in FIGS. 5 and 6, with the mask being removed over the endotracheal tube after the fiber optic probe has been removed.

Referring now to FIG. 6, mask 200 may be seen, having inflatable cuff 218 with a slightly larger inside diameter than that depicted in FIG. 5. Endotracheal tube 280 may be seen after it has been admitted through instrument port 214 such that endotracheal tube distal end 284 is positioned within larynx 290. An airtight seal may seal may be formed between inflatable cuff 218 and endotracheal tube 280. Positive pressure ventilation may thus be maintained within mask 200. Thus, the continuous flow of oxygen and general anesthesia gases may be maintained. In particular, even though voluntary breathing by the patient may have ceased, positive pressure ventilation gases may be provided through breathing circuit tube 212. FIG. 7 is a side, transverse, cross-sectional view, as in FIGS. 5 and 6, with the mask being removed over the endotracheal tube after the fiber optic probe has been removed;

Referring now to FIG. 7, mask 200 may be seen after removal from the patient's face. Inflatable cuff 218 may be controlled such that the inside diameter of instrument port 214 is at its maximum. In one embodiment, a syringe may be used to withdraw air through port 216, thereby evacuating most of the air from cuff 218. The fiber optic laryngoscope may be withdrawn, as illustrated in FIG. 7. Endotracheal tube proximal end 282 may typically include a connector having nominally a three-eighths inch (3/8") inside diameter and a five-eighths inch (5/8") outside diameter. Endotracheal tube proximal end 282 may also have a flange, which may increase the effective profile or outside diameter of the endotracheal tube proximal end. Instrument port 214 may be seen to have a maximum inside diameter sufficiently large to allow passage of the endotracheal tube proximal connector or coupling therethrough. Thus, the mask may be removed over the endotracheal tube.

It should be noted that the situation illustrated in FIG. 7 may well be the first time period in which positive pressure ventilation has been discontinued, since the mask was applied. This break in positive pressure ventilation and the delivery of general anesthesia gas may be very brief. In particular, the loss of positive pressure ventilation may be required only for the short period required for the proximal end of the endotracheal tube to pass through the opened instrument port. Breathing circuit 212 may be removed from the breathing circuit port 208 and coupled directly to endotracheal tube proximal end 282 in some embodiments. Endotracheal tube distal end at 284 may be inflated to form a tight seal to continue the positive pressure ventilation.

Referring again to FIG. 4, mask 200 may be applied to patient 202 in an ambulance, with a lid in place over instrument port 214. Breathing circuit 212 may represent a ventilation tube present in the ambulance. The same mask 200 may be seen in place in FIG. 5, with positive pressure ventilation being provided, most likely in a hospital emergency room. The same mask 200 is also present in FIG. 6, being removed only in FIG. 7, after the endotracheal tube has been positioned. Mask 200 may thus provide a continuous tight seal about the patient's face from an automobile accident site continuously through to an emergency or operating room after successful and careful placement of an endotracheal tube. Mask 200 may be seen to not require intermittent removal while an anesthesiologist attempts to insert a fiber optic laryngoscope before the patient desaturates and/or regains consciousness.

Referring again to FIG. 5, fiber optic laryngoscope 250 should be understood to represent any medical device shaft. Similarly, endotracheal tube 280 should be understood to also represent any suitable medical device shaft having a lumen through at least part of the shaft. Shaft distal tip 252 may be disposed within the trachea, or esophagus 292, or nasal cavity 294. Shaft 250 may be understood to perform any of a number of well-known procedures, including diagnostic and therapeutic procedures. This can include localized delivery of drugs and radiation. Biopsy samples may also be taken using appropriate shafts. Fiber optic tube 250 may be used to explore the lungs, stomach, and nasal cavity. Shaft distal tip 252 may also be used to cut and or cauterize tissue, in methods well-known to those skilled in the art. This can include, for example, procedures performed on the bile duct.

Experimental Results

Methods: An aperture 1.5 inches in diameter was created over the dome of an anesthesia face mask. An inflatable diaphragm, made of polyvinylchloride, was soldered to the periphery of the aperture. Inflation of the diaphragm with 10–15 cc of air completely closed the aperture and deflation opened the diaphragm. A bronchoscope was introduced through the mask aperture and the diaphragm inflated to provide an air tight seal around the bronchoscope. Once the trachea was identified, the diaphragm was partially deflated and size # 9 endotracheal tube was railroaded into place. Following intubation, the diaphragm was deflated and the mask removed. The intubation procedure using the mask was repeated at varying airway pressures while on pressure control ventilation (PCV). Air leak was defined as the difference between inspiratory and expiratory volume, expressed as a ratio of inspiratory minute ventilation. (MVI–MVE)/MVI. The results are summarized in Table 1. Using the mask, fiberoptic intubation was accomplished without difficulty at varying degrees of positive pressure ventilation. Even at high airway pressures, air leak was minimal and minute ventilation adequate.

TABLE 1

| PCV (cm) | 10 | 20 | 30 | 40 | 50 |
|---|---|---|---|---|---|
| Air Leak | 0.08 ± 0.10 | 0.13 ± 0.11 | 0.21 ± 0.09 | 0.23 ± 0.06 | 0.26 ± 0.15 |

Discussion: The mask described in this study permits insertion of larger devices (up to 1.5 inches) while maintaining an airtight seal during endoscopy and intubation.

What is claimed is:

1. A method for providing a breathable gas to a patient, the method comprising the steps of:
   providing a face mask having a first aperture and a second aperture, the first aperture having a controllably variable inside diameter, wherein the second aperture is in fluid communication with the breathable gas;
   placing the mask over the face of the patient;
   supplying the breathable gas to the patient through the second aperture;
   inserting a first shaft member through the first aperture;
   forming a seal between the first aperture and the inserted first shaft member; and
   advancing the first shaft member into either of the oral or nasal orifice of the patient while supplying the breathable gas to the patient.

2. A method for providing a breathable gas as in claim 1, wherein the first aperture has an inner wall defining the controllably variable inside diameter.

3. A method for providing a breathable gas as in claim 1, wherein the first aperture closing step includes forming an air-tight seal about the inserted first shaft member.

4. A method for providing a breathable gas as in claim 1, wherein the breathable gas supplying step includes supplying the breathable gas at a positive pressure within the mask to the patient.

5. A method for providing a breathable gas as in claim 4, wherein the breathable gas supplying step includes supplying the breathable gas which is enriched in oxygen relative to air.

6. A method for providing a breathable gas as in claim 4, wherein the breathable gas supplying step includes supplying an anesthetic agent in the breathable gas.

7. A method for providing a breathable gas as in claim 1, wherein the first shaft member is a laryngoscope and the method further includes identifying the trachea using the laryngoscope.

8. A method for providing a breathable gas as in claim 7, further comprising:
   providing a second shaft member having a lumen therethrough; and
   advancing the second shaft over the first shaft, through the first aperture and into the patient.

9. A method for providing a breathable gas as in claim 8, wherein the second shaft is an endotracheal tube, and the method further comprises:
   supplying the breathable gas through the endotracheal tube; and
   removing the mask from the face over the endotracheal tube.

10. A method for providing a breathable gas as in claim 9, wherein the endotracheal tube has a proximal end, and the removing step includes disconnecting the endotracheal tube from the breathable gas and passing the mask first aperture over the endotracheal tube proximal end.

11. A method for providing a breathable gas as in claim 8, wherein the first and second shaft members are advanced together through the first aperture.

12. A method for providing a breathable gas as in claim 7, wherein the inserting first shaft member step is preceded by a step including adjusting the first aperture inside diameter so as to be able large enough to receive the first shaft member therethrough, and the second shaft advancing step is preceded by adjusting the first aperture inside diameter so as to be large enough to receive the second shaft therethrough.

13. A method for providing a breathable gas as in claim 1, wherein the mask has an apex and the first aperture is closer to the apex than the second aperture.

14. A method for providing a breathable gas as in claim 1, wherein the supplying breathable gas step includes maintaining the breathable gas between the mask and face at a positive pressure, wherein the breathable gas includes an anesthetic agent, further comprising performing a medical procedure using the first shaft, wherein the medical procedure is selected from the group consisting of diagnostic and therapeutic medical procedures.

15. A method for providing a breathable gas as in claim 14, wherein the medical procedures are selected from the group consisting of examination and treatment of lesions of the nose, sinuses, mouth, larynx, pharynx, trachea, bronchi, esophagus and stomach.

16. A method for providing a breathable gas as in claim 14, wherein the first shaft is inserted into body conduits selected from the group consisting of the nasal cavities, the oral cavities, the trachea, and the esophagus.

17. A method for providing a breathable gas as in claim 1, wherein the supplying breathable gas step includes supplying an anesthetic agent.

18. A method for providing a breathable gas as in claim 1, wherein the supplying breathable gas step includes supplying an anesthetic agent through the second aperture while the first aperture is sealed against airflow, further comprising adjusting the first aperture inside diameter to accommodate passage of an endotracheal tube and advancing the endotracheal tube through the first aperture.

19. A face mask for placement on the face of a patient, the face mask comprising:
   a mask wall having a generally concave interior shape, the mask wall having a first aperture therethrough and a second aperture therethrough, wherein the first aperture has an adjustable inside diameter.

20. A face mask as in claim 19, wherein the first aperture is disposed within a raised lip having an inner wall, wherein the adjustable inside diameter aspect includes an inwardly movable wall.

21. A face mask as in claim 19, wherein the wall is part of an inflatable envelope disposed within the first aperture.

22. A face mask as in claim 19, wherein the first aperture has a wall defining the aperture, wherein the wall has an inflatable envelope disposed within, such that inflating the envelope decreases the inside diameter of the first aperture.

23. A face mask as in claim 19, wherein the first aperture has an inner wall defined by a plurality of members, wherein the members have an open position and a closed position, wherein the members are movable between the open and the closed position for decreasing the first aperture inside diameter.

24. A face mask as in claim 23, wherein the plurality of members are inflatable balloon members, such that inflating the members decreases the inside diameter.

25. A face mask as in claim 23, wherein the plurality of members are iris members which cooperate to decrease the first aperture inside diameter.

26. A face mask as in claim 19, wherein the face mask wall has an apex, wherein the first aperture is disposed closer to the apex than the second aperture.

27. A face mask as in claim 19, wherein the mask has an apex, wherein the first aperture is disposed within the apex.

28. A face mask as in claim 19, wherein the first aperture has a maximum inside diameter, wherein the maximum inside diameter is at least about 3/8 inch.

29. A face mask as in claim 19, wherein the first aperture has a maximum inside diameter, wherein the maximum inside diameter is at least about 5/8 inch.

30. A face mask as in claim 19, wherein the first aperture had a maximum inside diameter, wherein the maximum inside diameter is at least about 1 inch.

31. A face mask for providing positive pressure ventilation to a patient, a face mask comprising:

a face mask wall for extending over the mouth and nose of the patient;

the face mask wall having a first aperture therethrough and a second aperture therethrough, wherein the first aperture has a seal therein for providing a controllably variable inside diameter to the first aperture.

32. A face mask as in claim 31, wherein the seal includes at least one inflatable balloon, such that inflating the at least one balloon decreases the inside diameter of the first aperture.

33. A face mask as in claim 31, wherein the first aperture seal includes an adjustable iris.

* * * * *